United States Patent
Papademetriou et al.

(10) Patent No.: US 6,339,470 B1
(45) Date of Patent: Jan. 15, 2002

(54) APPARATUS AND METHOD FOR ALIGNING AN ENERGY BEAM

(75) Inventors: Stephanos Papademetriou, Sunnyvale; Victor C. Esch, San Francisco, both of CA (US)

(73) Assignee: EndoVasix, Inc., Belmont, CA (US)

( * ) Notice: Subject to any disclaimer, the term of this patent is extended or adjusted under 35 U.S.C. 154(b) by 0 days.

(21) Appl. No.: 09/299,415

(22) Filed: Apr. 26, 1999

(51) Int. Cl.[7] .............................................. G01B 11/26
(52) U.S. Cl. ........................ 356/153; 356/138; 356/73.1
(58) Field of Search ................... 356/153, 138, 356/73.1; 385/135, 136; 606/7

(56) References Cited

U.S. PATENT DOCUMENTS

| | | | |
|---|---|---|---|
| 4,084,182 A | | 4/1978 | Maiman |
| 4,538,613 A | | 9/1985 | Rosenberg |
| 4,798,449 A | | 1/1989 | Vichon et al. |
| 4,875,969 A | | 10/1989 | Hsu et al. |
| 4,880,494 A | | 11/1989 | Kaukeinen et al. |
| 4,911,526 A | | 3/1990 | Hsu et al. |
| 4,913,142 A | | 4/1990 | Kittrell et al. |
| 4,923,275 A | | 5/1990 | Kaukeinen |
| 4,957,342 A | | 9/1990 | Boudreau et al. |
| 4,994,059 A | * | 2/1991 | Kosa et al. ................ 356/73.1 |
| 5,024,504 A | | 6/1991 | Boudreau et al. |
| 5,034,010 A | | 7/1991 | Kittrell et al. |
| 5,121,457 A | | 6/1992 | Foley et al. |
| 5,127,068 A | | 6/1992 | Baer et al. |
| 5,153,782 A | | 10/1992 | Crone et al. |
| 5,192,278 A | | 3/1993 | Hayes et al. |
| 5,209,748 A | | 5/1993 | Daikuzuno |
| 5,214,730 A | | 5/1993 | Nagasawa et al. |
| 5,290,277 A | | 3/1994 | Vercimak et al. |
| 5,394,495 A | | 2/1995 | Booth et al. |
| 5,400,428 A | | 3/1995 | Grace |
| 5,420,954 A | | 5/1995 | Swirhun et al. |
| 5,519,798 A | | 5/1996 | Shahid et al. |
| 5,559,915 A | | 9/1996 | Deveau |
| 5,598,494 A | | 1/1997 | Behrmann et al. |
| 5,620,634 A | | 4/1997 | Shahid |
| 5,631,988 A | | 5/1997 | Swirhun et al. |
| 5,751,835 A | | 5/1998 | Topping et al. |
| 5,859,947 A | * | 1/1999 | Kiryuscheva et al. ....... 385/136 |
| 5,946,099 A | * | 8/1999 | Ota et al. .................. 356/375 |

FOREIGN PATENT DOCUMENTS

| | | |
|---|---|---|
| EP | 0 574 686 A2 | 5/1993 |
| EP | 0249237 | 9/1993 |
| JP | 07027942 | 1/1995 |
| JP | 11014864 | 1/1999 |
| WO | 91/02994 | 3/1991 |

OTHER PUBLICATIONS

"Wave Optics Specialty Fiber Optic Products" 1997 catalog, p. 32.
Fiberoptic Product News, "The Global Source for Fiberoptic Technology and Applications" (unknown date), two pages.
J. Senior, *Optical Fiber Comunications: Principles and Practice*, pp. 144–173, ©1985 Prentice–Hall International., Inc., London.
International Search Report for PCT/US00/09345 dated Aug. 21, 2000.
International Search Report for corresponding PCT application No. PCT/US00/09345 dated Nov. 13, 2000.

* cited by examiner

*Primary Examiner*—Frank G. Font
*Assistant Examiner*—Roy M. Punnoose
(74) *Attorney, Agent, or Firm*—Skjerven Morrill Macpherson LLP; K. Alison de Runtz

(57) ABSTRACT

An apparatus, including a light detecting means, determines the actual position of an optical fiber array having one or more, but fewer than all, short fibers by detecting light transmitted through the short fiber(s) as a laser beam is horizontally and/or vertically scanned across the proximal fiber end(s). The fiber array is attached to an alignment block that facilitates delivery of the array to an accurate positioning means comprising two substantially parallel dowels.

5 Claims, 4 Drawing Sheets

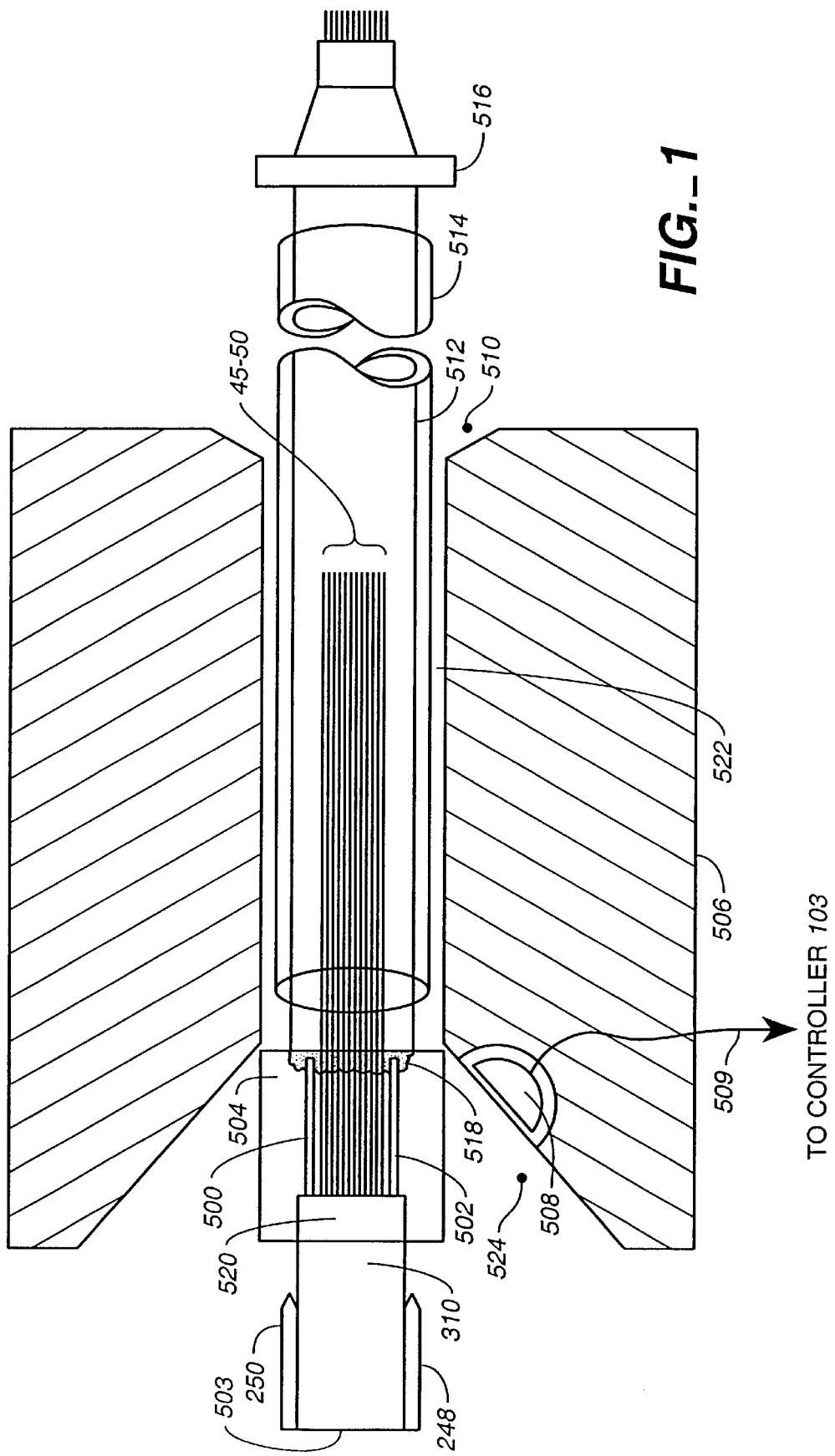
FIG._1

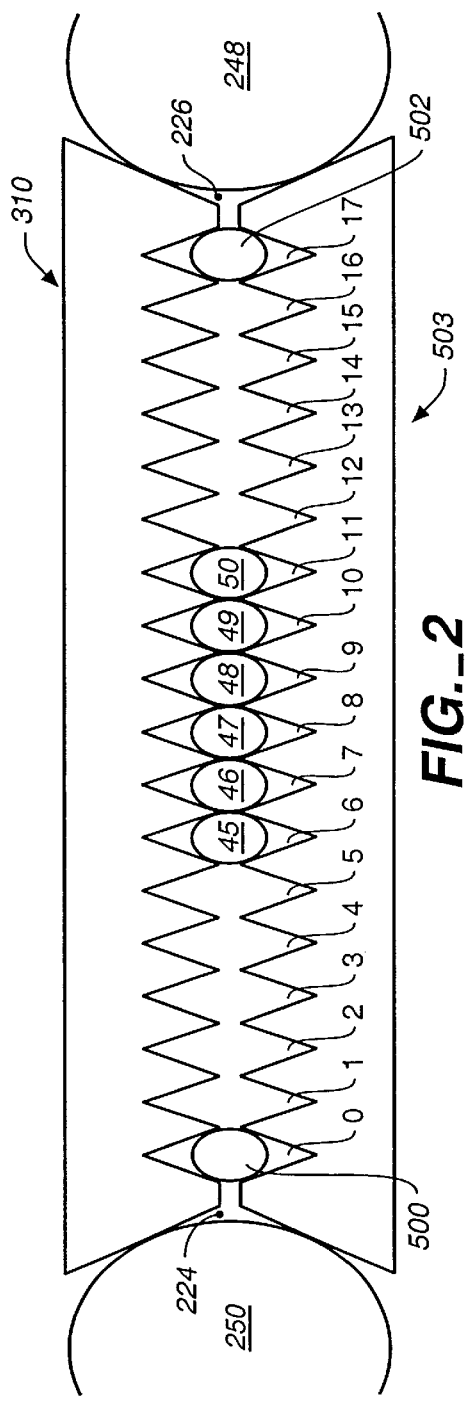
FIG._2
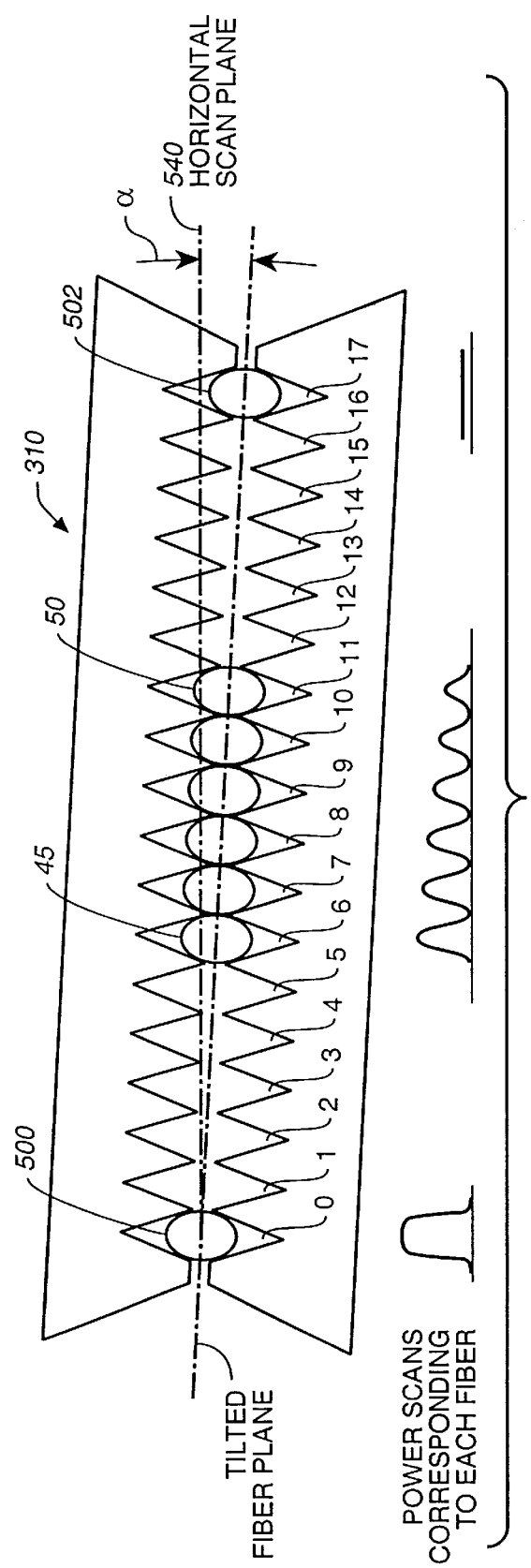
FIG._5

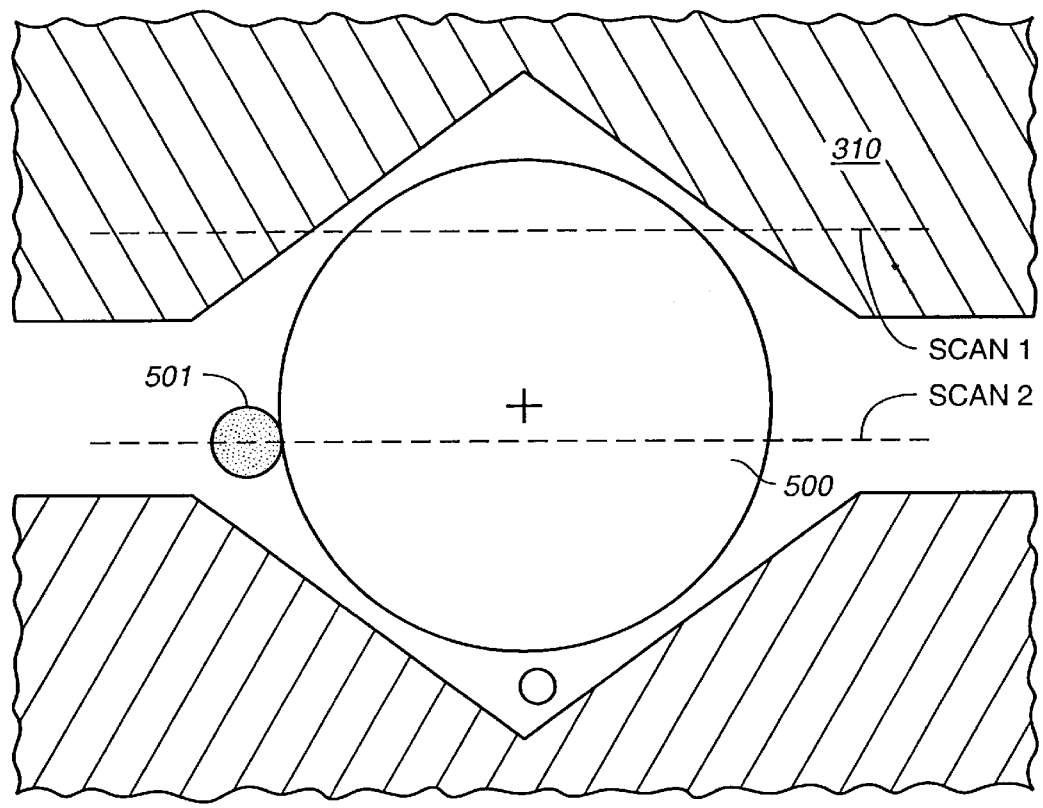
FIG._3A
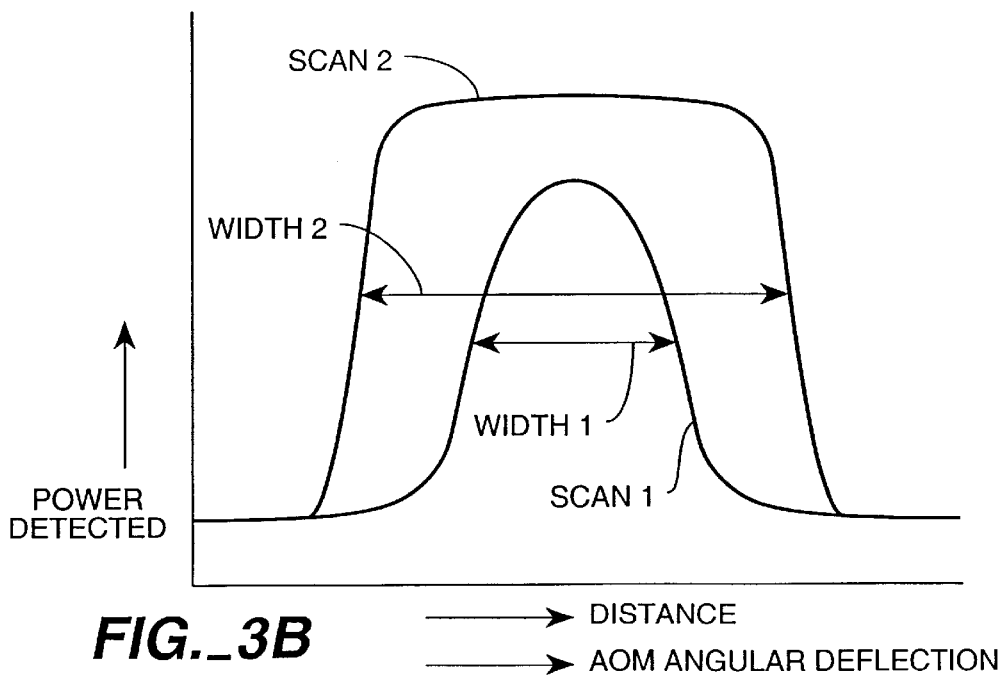
FIG._3B

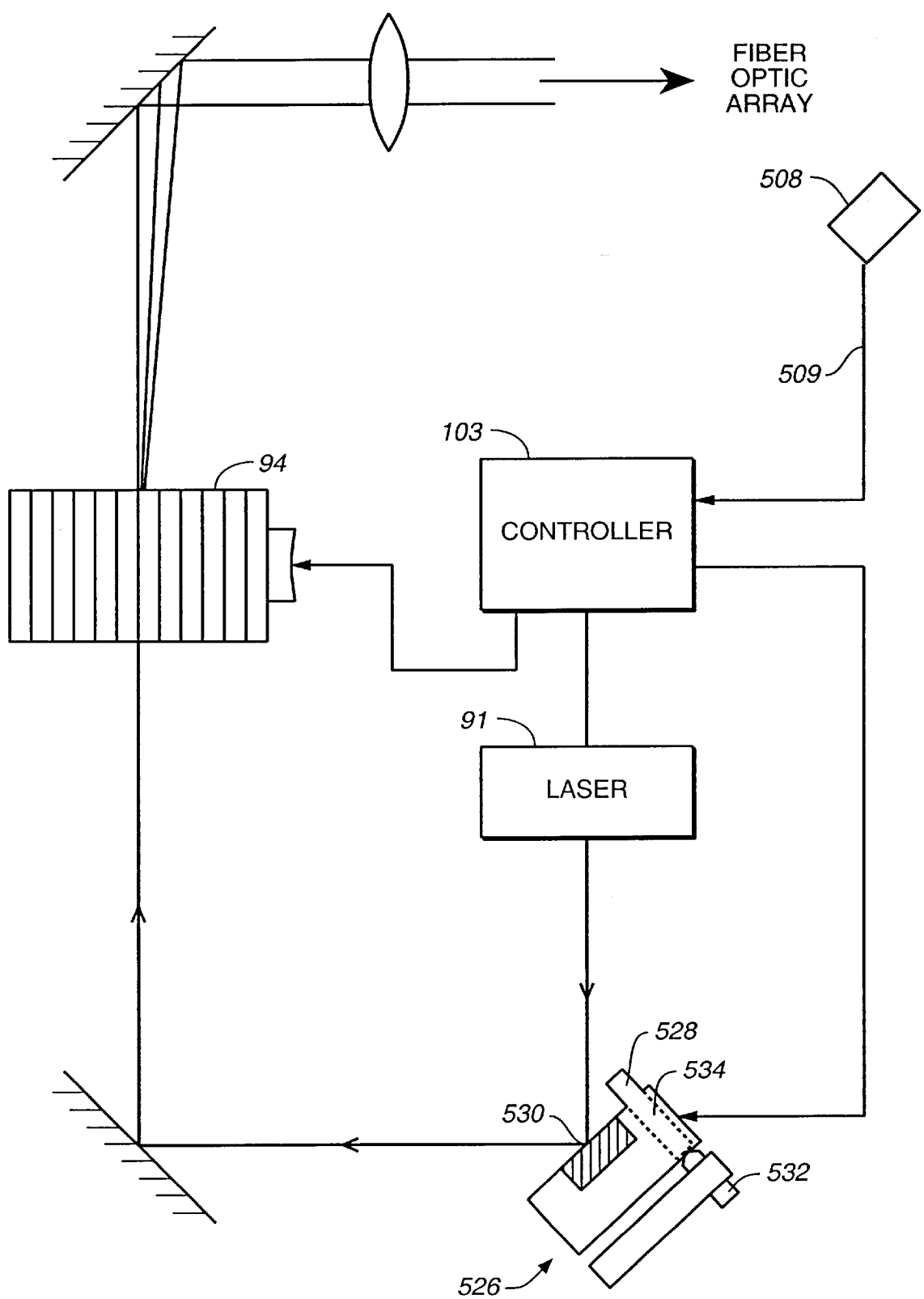
FIG._4

APPARATUS AND METHOD FOR ALIGNING AN ENERGY BEAM

BACKGROUND OF THE INVENTION

This patent application is related to U.S. patent application Ser. No. 09/113,700 (hereinafter the "'700 application"), entitled "Apparatus and Method for Delivering Radiation Energy," filed on Jul. 10, 1998. The entirety of the '700 application is herein incorporated by reference.

Described in the '700 application is an apparatus and method for accurately positioning an array of fibers in space so that a free beam of radiation may reproducibly be directed to each fiber in the array. It has been discovered that a number of external factors can contribute to misalignment of the fibers with the free beam of radiation notwithstanding this structure. These can include, among other things, the apparatus being jarred during use or shipping, misalignment of the fiber array in the tuning fork assembly, misalignment of the predetermined initial firing setting of the laser beam, and potential manufacturing defects in the silicon cassette that contribute to slight misalignment. Yet a laser system ideally will not become unusable simply because the laser beam is unable initially to impinge directly upon each active treatment optical fiber in the fiber array due to misalignment. Rather, it is preferable to have the laser apparatus capable of discovering the exact location of the optical fiber array, and thus of each fiber in the array, even if the array is misaligned to some extent.

Manual adjustments of positioning mechanisms such as X-Y-Z tables, or analyses of backscattered light from the various proximal surfaces of an optical fiber cassette to determine the location of an optical fiber—i.e., retroreflection—have previously been required at the outset of a procedure to ensure that a free laser beam of the kind disclosed in the '700 application accurately impinges on a series of optical fibers in a linear array. Such adjustments were necessary so that once the laser was used for treatment, the laser could accurately and reproducibly locate each optical fiber without further major adjustments. However, it is preferable to eliminate most, if not all, of the required manual adjustments by having a laser system capable of verifying the location of the fiber array before treatment and adjusting itself accordingly, or of determining that the fiber array is unusable for whatever reason. The inventions disclosed herein enable alignment of a free beam of radiation with a fiber array notwithstanding slight misalignment of the array. The inventions disclosed in this patent application contribute to a laser apparatus' capability to discover the position of one or more fibers in a fiber array, in order accurately and reproducibly to deliver a free radiation beam to that array.

SUMMARY OF THE INVENTION

Briefly and generally, an optical fiber cassette with multiple optical fibers is constructed with one or more, but fewer than all, optical fibers terminating short of the far distal ends of the remaining fibers. An apparatus including a light detecting means determines the actual position of the fiber cassette and/or verifies that the cassette is accurately positioned by detecting light transmitted through the shorter fiber(s) as a laser beam is horizontally and/or vertically scanned across the proximal fiber end(s). Positioning (or registration) fiber(s) may terminate inside an alignment block attached to the fiber cassette that facilitates delivery of the cassette to an accurate positioning means comprising two substantially parallel pins.

Additional objects, features and advantages of the various aspects of the present invention will be better understood from the following description of its preferred embodiments, which description should be taken in conjunction with the accompanying drawings.

BRIEF DESCRIPTION OF THE DRAWINGS

FIG. 1 is schematic of a preferred embodiment of the fiber cassette/alignment block/proximal catheter assembly invention.

FIG. 2 is a simplified view of the proximal end of the embodiment depicted in FIG. 1, showing positioning fibers and active treatment fibers.

FIG. 3A depicts a magnified view of the first positioning fiber. FIG. 3B depicts the data sets produced from the scans shown on FIG. 3A.

FIG. 4 shows an electro-optical diagram of an embodiment of the present invention.

FIG. 5 depicts a non-horizontally positioned fiber array, and illustrative data sets that might be produced by a horizontal alignment scan of a laser beam across the entire array.

DESCRIPTION OF THE PREFERRED EMBODIMENTS

This discussion of a preferred embodiment of the invention will use as an example an array of 18 possible fiber channels, numbered 0 to 17, in a lithographically-etched fiber cassette of the type disclosed in the '700 application and shown in a simplified manner in FIG. 2. A fiber cassette of this type is manufactured as previously described, and the desired number of optical fibers is positioned within the array. Preferably the active fibers in an array are positioned around the center point of the array. Thus, for the six active optical fiber array shown in FIGS. 1 and 2, optical fibers 45–50 would occupy the fiber channels numbered 6 through 11. The six channels on either side of the active fiber set preferably would not contain any active fibers. Although this example identifies the registration fibers as occupying the outermost positions in the 18-channel fiber cassette, it should be understood that outermost positioning is not required. The important part is that deflecting means, such as an acousto-optic modulator acousto-optic modulator (AOM), is able efficiently to deflect the laser beam onto and across the width of each registration fiber. However, the further away the registration fiber(s) are from each other and from the center of the fiber cassette, the more accurate is the determination of whether the fiber cassette is horizontally positioned, as is further described below. Furthermore, it will be clear to one of skill in the art that certain of the active fibers also may be used to determine the cassette's alignment, instead of using one or more "alignment-dedicated" registration fibers, as long as the fiber cassette/catheter device is positioned so as to permit the detection of transmitted light during the positioning procedure. Various practical considerations, however, such as desired sterility of the distal portion of the optical fibers, would have to be addressed for such implementation.

Although in this example, there are 18 fiber channels available, only a maximum of 16 possibly active optical fibers may be used for treatment because the outermost channels (channel numbers 0 and 17) are reserved for use in either determining the actual position of the fiber array with respect to a free laser beam, or ensuring that the fiber array is correctly positioned with respect thereto. Preferably, only a maximum of 14 or even 12 active fibers would be used, to provide some spacing between the positioning fibers 500 and 502 and the actual active fiber array 45–50. This spacing permits the laser beam to have freedom to move in the vicinity of the positioning fiber to locate its center, as described below, without impinging on one of the active fibers and potentially causing unwanted transmission of the laser beam through one of the active fibers.

Each outermost positioning fiber is positioned within the proximal portion of the fiber cassette in the same manner as the active fibers. However, the distal portion of each positioning fiber does not extend down the length of the delivery apparatus, as do the active treatment fibers. Instead, the distal end of each positioning fiber is located such that light transmitted through that fiber can be detected by a light- or energy-sensing means 508, such as a photodiode or other photosensor positioned in the vicinity of the distal end of the fiber cassette 310.

While the fiber cassette can be positioned directly by hand between the pins 248 and 250 in the twin tower structure (not shown) disclosed in the '700 application, some sort of remote delivery mechanism might be used, if desired. A simple such mechanism may consist of a small plastic (e.g., ABS, Teflon) alignment block 504 attached to the distal end of the fiber cassette 310. This block has a hollow, longitudinal center, through which all of the optical fibers pass, and has a longitudinal slot on one face so that the block 504 can be attached to the fiber cassette 310 around the optical fiber strands. To facilitate attachment to the fiber cassette, the block may also have a recessed slot 520 in its proximal face into which the distal end of the fiber cassette is glued. For a fiber cassette of about 0.5 cm×1 cm, for example, a slot about 3 mm deep or greater has proven satisfactory to ensure proper positioning in the plastic block. A shallower slot has been found to contribute to irregular reproducibility of the cassette-block combination. The block 504 is wider and higher than the silicon cassette 310, and much deeper than the recessed attachment slot.

Returning to the discussion of the positioning fibers, FIG. 1 shows each positioning fiber 500 and 502 terminating within the distal portion of the alignment block 504. All of the fibers are secured in the distal portion of the alignment block with a mixture 518 of glue and a scattering medium, typically microparticles of some material having a refractive index different than—typically higher than—the glue, such as glass, aluminum oxide, sapphire or ground silica. When light is transmitted through a positioning fiber, the scattering material scatters the light, which in turn is detected by the photosensor 508. A scattering medium is used in mixture 518 to desensitize the positioning of the photosensor. Alternatively, instead of terminating within the glue/scattering medium mixture 518, the fiber cassette could be constructed so that the positioning fibers exit the cassette/alignment block combination and loop back into the mixture 518 where they are secured, or even loop over to the light detection means 508. The important part of the location of the distal tips of the positioning fibers is that transmitted light is detectable by the light detecting means 508. One other alternative would be to have a single registration fiber with its proximal end positioned in a first registration position in the cassette and its distal end—essentially a second "proximal" end—looped back to the cassette and mounted in a second registration position. In this construction, light delivered into the first proximal end would be detected when transmitted from the second end, and vice versa, by one or more light detection means in the vicinity of the proximal face of the fiber cassette.

The distal portion of the alignment block 504 also houses a flexible plastic tube 512 (e.g., made of C-Flex) that surrounds the optical fibers 45–50 to protect them from accidental breakage. The block is sized to fit within a long alignment channel 522 having one end remote from, and one end proximal to, the pins 248 and 250 for holding the fiber cassette 310. The channel 522 may be formed out of a nonyielding material 506, such as a hard polymer or plastic. The channel 522 desirably is flanged at both ends, and sized to tight tolerances relative to the block, so that the cassette/block combination can hold a relatively constant position in the channel during travel towards the pins 248 and 250. A user may insert the cassette/block combination into the entry port 510, typically on the exterior of the laser unit. The external edge of the entry port 510 is flanged to direct the cassette and block into the port. Once inserted, the user may need to use some sort of mechanism to push the cassette into place, such as a plastic straw 514, surrounding tube 512 and fibers 45–50, or a rod or similar pushing means to push the plastic block/cassette down the length of the channel 522 until it reaches the outlet port 524 of the channel. While possible, it is preferable not to directly mechanically couple the pushing means, such as the straw 514, to the alignment block 504 or the flange 516. Direct mechanical coupling of the pushing means can create undesired forces on the fiber cassette and alignment block if the pushing means—extending into the external environment—is knocked or bumped, even accidentally, during a procedure. Such external forces, conveyed to the alignment apparatus through the pushing means could jar an otherwise satisfactorily-positioned cassette out of alignment or can damage the various structures used to position the fiber array in space and/or the apparatus used to deliver laser energy to a treatment site. The outlet port 524 is positioned relative to the dowels 248 and 250 on the twin tower assembly (disclosed in the '700 application) such that as the block reaches the far end of the channel, the grooves 224 and 226 in the cassette are roughly aligned with the dowel tips 250 and 248, respectively. The outlet port 524 is flanged such that when the cassette 310 was properly positioned between the dowels 248 and 250, and locked into place with the shutter, the alignment block 504 is no longer constrained by the channel 522. This lack of ultimate constraint by the channel 522 helps to prevent the fiber cassette 310 from being stressed if there is an initial slight misalignment of the channel with the dowels tips as the cassette approaches the dowels. (The stress would result from being constrained by both the dowels and the channel at the same time). The light detecting means 508 used to assist in the alignment procedure using the positioning fibers may be located in the proximal flanged area 524, as shown in FIG. 1. A distance of about 1-mm between the detection means and the cassette have proven satisfactory to detect the scattered light emitted from the positioning fibers during alignment, as is described next. Flange 516 may be added to the proximal section of the optical fiber sheath (or catheter) so the sheath can be locked into place using a clamp or other locking mechanism, to avoid the device accidentally being pulled out of the laser system during use. A means for withdrawing the fiber cassette from between the dowels and back through channel 522, such as a flexible but relatively unstretchable nitinol wire (not shown), may be attached to the alignment block 504 to extend between the block and flange 516, to facilitate removal of the cassette/block combination while minimizing the potential for breaking any of the optical fibers. Preferably, however, this means for withdrawing should be flexible enough so as not to transfer to the alignment block, any undesirable external forces, as described above.

To begin the laser beam alignment procedure, the fiber cassette 310 is positioned in the twin-tower apparatus between the dowels 248 and 250 so that the proximal facet 503 lies at least substantially within the focal plane of the optical assembly used to deliver the laser beam to the optical fibers, part of which is shown in FIG. 4. Once the laser beam to be aligned is selected, the incoming laser beam is then scanned by the AOM 94 (FIG. 4) from an initial position—typically determined and set by the manufacturer—horizontally across where the first outermost alignment fiber 500 in the fiber optic array should be located. Because the beam is scanned using only the AOM 94 at this point, the beam should travel in a singular planar path across this first position. Scans 1 and 2 shown on FIG. 3A are examples of such initial scans. The increment of travel of successive laser beam firings during the scanning procedure will affect the speed at which the procedure is completed: the smaller the increment of movement (corresponding to the increment in the angular deflection of the beam produced by the AOM), the longer the procedure will take; the larger the incremental movement, the shorter is the period of time required to conduct the scan. However, the more movement per increment, the potentially less accurate is the ultimate alignment. The user should pick increments to best serve his needs depending on the desired degree of accuracy and speed. The path length of the first scan can either be preset to be a certain distance (equaling a certain number of increments) that should be greater than the optical fiber width, or can be determined by the width of the data set produced, and thus can be controlled to terminate after no more light is transmitted down fiber 500.

As the laser beam begins to impinge upon the surface of the optical fiber 500, light is transmitted through the fiber 500 to its distal end buried in the glue/scattering material mixture 518 at the distal end of the alignment block 504. The transmitted light is scattered and is detected by the photosensor 508 positioned in the flanged wall of the delivery channel 522. The greater the degree of impingement, the more light is transmitted and thus the more light is scattered, thereby increasing the amount of light detected by the photosensor 508. FIG. 3B depicts two typical data sets generated from scans across a positioning fiber 500. Each curve represents the relationship between power transmitted through the positioning fiber and detected by the photosensor 508 against incremental position of the laser beam impinging upon the positioning fiber. Scan 2 depicts a scan across the centerline of the fiber, whereas Scan 1 represents a scan across a shorter chord of the same fiber. The width (full width at half maximum, or FWHM) of each data set provides information about the width of the portion of the fiber scanned. As shown by the data set corresponding to Scan 1, the closer the scan is to the edge of the fiber, the more interference with light transmission there is, the narrower the data curve produced and the smaller the maximum degree of light transmission detected. The shapes of the curves in FIG. 3B are dependent upon the cross-sectional size of the laser beam relative to the fiber diameter. More specifically, for example, the more vertical portions of the Scan 2 data set evidence that the spot size 501 of the laser beam is much smaller than the diameter of the fiber 500 being scanned (e.g., a spot size of less than about 15 microns for a fiber diameter of greater than about 50 microns). If the beam diameter were to approach the fiber diameter, the more interference would be generated at the edges of the fiber during the positioning scan, and thus the less steep would be the transition zones of the Scan 2 data set. Alternatively, as the ratio of the spot size diameter to fiber diameter approaches zero, the steeper would be the transition zones of a data set. If no transmitted light is detected during an entire scan across fiber 500, another scan or scans may be conducted, or the fiber cassette may be rejected out of hand as unusable.

The alignment procedure may be stopped at this point, the center of the data set determined, and the laser controlled to operate so that the laser beam will impinge upon that data set centerpoint. However, at this point in the procedure, there is no certainty that the centerpoint of the first scan is actually the fiber's centerpoint, so as to ensure maximum transmission of the laser beam through the active fibers once the device is activated for treatment, unless the width of the scan's data set equals or exceeds an acceptable width indicating that the scan was conducted at least substantially close to, if not directly upon, the fiber's diameter. Thus, more than one scan is usually desirable. The alternatives for scanning the first positioning fiber multiple times are many, including multiple vertically-indexed horizontal scans across the face of the fiber, another single scan vertically across the face of the fiber, multiple horizontally-indexed vertical scans, or a combination of any of these.

For a second horizontal scan to be performed, the laser beam first can be vertically adjusted so that the second horizontal scan can be performed on a chord different from the first scan and its data compared to the data of the first scan. Again, vertical increments may be chosen by taking into account the same considerations as above. Vertical adjusting means 526, such as a kinematic mount, shown in FIG. 4, achieves vertical adjustment of the laser beam delivered to the fiber array by adjusting the angle of the mirror 530 attached to vertical adjustment means 526. Although a kinematic mount is preferred as vertical adjustment means 526, any mechanism that can incrementally adjust the angle of a mirror may be used, such as a galvanometer. Alternatively, another AOM could be used to deflect vertically the beam. While the vertical adjustment means 526 may be adjusted manually by adjusting one of the adjustment screws 532, automatic adjustment may be achieved by having the pertinent adjustment screw impinge upon a piezoelectric stack 534. This stack will expand as voltage is applied, thereby biasing the adjustment screw 532, incrementally changing the angle of the mount table, and so changing the angle of the mirror 530. The higher the voltage applied to the piezoelectric stack, the greater the degree of expansion and thus the change in the angle of the mirror 530. Voltages are selected to adjust the mirror so that the laser beam is adjusted the desired increment. Once the laser beam is vertically adjusted to the desired height, the horizontal scan is repeated, either in the same direction as the first scan or backwards across the fiber, thereby producing another data set of detected transmitted power versus distance traveled (of AOM angular deflection).

Alternatively, as mentioned above, a vertical scan may be conducted of the same fiber. In this example, a vertical scan may be conducted by repeatedly incrementally adjusting the angle of mirror 530 by adjusting the voltage delivered to the piezoelectric stack 534, and so moving the laser beam vertically down the fiber face in a manner similar to how the beam was moved horizontally across the face of the fiber using the AOM. However, while an AOM typically has a wide angular range of laser beam deflection, such that it can scan a laser beam across a single optical fiber face without difficulty, vertical movement of a laser beam through expansion of a piezoelectric stack is limited by the size of the stack. The longer the desired vertical path of beam movement, the larger must be the piezoelectric stack. Of course, as the size of the stack increases to accommodate a longer vertical path, so do the size and cost of the kinematic mount. The kinematic mount 526 is depicted with a modification 528 to accommodate a long piezoelectric stack 534. To avoid requiring a disproportionately large piezoelectric stack, it may be desirable during a vertical scan to cause the laser beam to travel a vertical chord shorter than the fiber's diameter. In other words, the closer the chord is to the edge of the optical fiber, the shorter the chord length to be traveled by the laser beam, and thus the smaller the piezoelectric stack need be to accomplish the desired scan.

After the midpoint of the first horizontal scan and the midpoint of the first vertical scan have been determined, the midpoint of the first outermost fiber should be known. If desired, another scan can verify that the center point of the fiber has been accurately located by, e.g., performing another horizontal scan through the midpoint of the vertical scan and verifying that the width of the data set generated corresponds to the expected value for the width of the fiber being scanned.

At this point of the method, the location of the centerpoint of the first fiber has been found. Because the distance between adjacent centerpoints of each channel in the fiber cassette 310—and thus the distance between the centerpoints of adjacent fibers—is known (preferably about 75 microns), due to the precise lithographic etching process used to manufacture the cassette, and because the controller 103 is aware (through manual data input or from reading a microchip on the catheter) of the number and spatial arrangement of active fibers in the cassette, the distances from the positioning fiber's centerpoint to the active fibers' centerpoints are known. However, accurate delivery of a free laser beam to each of the active fibers cannot yet be assured, due to the fact that the fiber cassette 310 as a whole may not be truly horizontal, as depicted in FIG. 5. If the fiber array is tilted away from horizontal, however slightly, the distance between the point the laser beam will actually impinge upon each fiber (if at all) and the centerpoint of each fiber will increase for fibers further away from the first fiber. FIG. 5 depicts an example in which the fiber cassette is tilted an angle a from horizontal, such that a scan of the laser beam on a plane 540 corresponding to the center point of alignment fiber 500 would in fact barely impinge upon fiber 50, and would not impinge at all upon registration fiber 502, indicating the cassette is out of alignment. Note that although scans are depicted for each fiber in the array (for illustrative purposes), only fibers 500 and 502 would be scanned in this preferred embodiment of the invention.

Thus, to better ensure actual accurate impingement of the laser beam on each fiber of the array, another positioning scanning procedure may be conducted on the fiber 502 occupying the other outermost position in the array. Verifying the position of this second positioning fiber 502 can be conducted in any number of ways, including any number of horizontal and vertical scans, as described above. However, since the actual centerpoint of fiber 502 relative to the fiber cassette will be known based on the known etch dimensions, it may be desirable only to determine whether the fiber cassette 310 is, in fact, horizontal or, if not, to what extent it is tilted.

One method of verifying whether the entire fiber array is substantially horizontal is to scan the second outermost fiber 502 with a laser beam on the same level as the centerpoint of the first outermost fiber—i.e., using the AOM with the piezoelectric stack 526 adjusted to provide a vertical setting corresponding to the vertical position of the centerpoint of the first positioning fiber 500. If the width of the data set produced from this scan falls within a certain tolerance of the actual width of the optical fiber, then the array can be deemed to be horizontal and no further scans may be necessary. Within a "certain tolerance" of the actual width of the optical fiber is acceptable because of the difference in sizes between the width of the laser beam itself and the width of an optical fiber. Since a typical laser beam does not necessarily have to impinge exactly upon the centerpoint for its energy to be delivered to the fiber without appreciable losses, slight tilt (e.g., on the order of microns) of the fiber cassette may be tolerable.

If the data set produced from this scan demonstrates that the array is, in fact, not horizontally positioned, however, due to the width of the data set being below specification, information such as an audible or visible readout can inform the user that the insertion of the fiber cassette has failed, and that the cassette should be reinserted or a new cassette used. Alternatively, instead of rejecting the cassette, the centerpoint of the fiber can be located as described above using one or more horizontal or vertical scans. Once the location of the centerpoint of the second outermost fiber is known, the relative horizontal and vertical positioning of each of the outermost fibers is known, and thus the relative horizontal and vertical positions of each of the optical fibers in the array will be known from trigonometry. If desired, the laser beam can then be delivered to each of the optical fibers in the array by the controller 103 adjusting both the horizontal distance from the centerpoint of the first outermost fiber (with the AOM) and the vertical distance from the centerpoint of the first outermost fiber (with the piezoelectric stack on the kinematic mount). Note, however, that the piezoelectric stack will limit the speed with which the laser beam can be adjusted between adjacent fibers, since the expansion of the stack takes a longer period of time than is required for the AOM to change the angle of the scanning beam. Alternatively, if both horizontal and vertical positioning is desired to locate each fiber in the array, any other means for scanning the laser beam can be used to accurately vertically position the laser beam on each fiber, such as a second AOM, a galvanometer (with its speed limitations), or a polygonal mirror.

If a laser system utilizes more than a single laser beam, such as the system disclosed in the '700 application, each laser beam can be aligned with the fiber array in the manner described herein, to ensure accurate delivery of each beam to each active fiber in the array. The alignment methods described and disclosed herein may be implemented through any number of hardware and/or software arrangements, which are within the realm of skill in the art.

Although in this preferred embodiment, the outermost positions of the array were used for the positioning fibers, it will be clear to one of skill in the art that this positioning scanning method may be performed on any particular fiber of interest.

A major advantage of this procedure is that the location of each fiber is determined by analyzing not light backscattered from a fiber surface, but by analyzing power actually transmitted through the fiber. The detection of backscattered light, and the resulting analysis of whether the backscatter is due to a surface of the cassette or hardened glue or the glue-fiber interface or the fiber surface itself, whether or not well polished, is often not straightforward. Detection of transmitted light to determine accurate alignment, however, obviously depends on transmission of light through the fiber and thus eliminates many of the variables that affect analysis of backscattered light for alignment.

Although the various aspects of the present invention have been described with respect to their preferred embodiments, it will be understood that the invention is entitled to protection within the full scope of the appended claims.

It is claimed:

1. A method for delivering a beam of energy to an optical fiber in a fiber array, comprising:

positioning a fiber array having at least one active optical fiber and at least one positioning fiber, each active fiber and each positioning fiber having a proximal and a distal end;

scanning a first beam of radiation energy across the proximal end of the at least one positioning fiber along at least a first path having increments;

detecting radiation transmitted through the at least one positioning fiber and producing a signal of transmitted radiation for each increment of the first path for which transmitted radiation is detected; and determining a midpoint of the increments of the first path for which transmitted radiation is detected; and delivering a second beam of radiation energy to the at least one active optical fiber in the fiber array.

2. The method of claim 1, further comprising adding (i) a known distance from a midpoint of the at least one positioning fiber to a midpoint of each active fiber and (ii) the midpoint of the increments of the first path.

3. A method for delivering a beam of radiation energy to an optical fiber in a fiber array, comprising:

positioning a fiber array having at least one active optical fiber and at least one positioning fiber, each active fiber and each positioning fiber having a proximal and a distal end;

scanning a first beam of radiation energy across the proximal end of the at least one positioning fiber along at least a first path having increments;

detecting radiation transmitted through the at least one positioning fiber and producing a signal of transmitted radiation for each increment of the first path for which radiation is detected;

scanning the first beam of radiation energy across the proximal end of the at least one positioning fiber along a second path having increments;

detecting radiation transmitted through the at least one positioning fiber and producing a radiation signal of transmitted radiation for each increment of the second path for which radiation is detected;

determining a centerpoint of the at least one positioning fiber; and delivering a second beam of radiation energy to the at least one active fiber in the fiber array.

4. The method of claim 3, wherein the second path is substantially perpendicular to the first path.

5. The method of claim 3 or 4, further comprising scanning the first beam of energy across a second positioning fiber to determine whether the fiber array is horizontally positioned.

* * * * *